(12) United States Patent
Taniuchi

(10) Patent No.: US 6,169,060 B1
(45) Date of Patent: Jan. 2, 2001

(54) CLEANSER COMPOSITION INCLUDING A MIXTURE OF ANIONIC, NONIONIC, AND AMPHOTERIC SURFACTANTS

(75) Inventor: Shinji Taniuchi, Sukagawa (JP)

(73) Assignee: Johnson & Johnson Kabushiki Kaisha (JP)

(*) Notice: Under 35 U.S.C. 154(b), the term of this patent shall be extended for 0 days.

(21) Appl. No.: 09/454,877

(22) Filed: Dec. 3, 1999

(30) Foreign Application Priority Data

Dec. 11, 1998 (JP) .................................................. 10-353452

(51) Int. Cl.[7] ................................ C11D 1/12; C11D 1/29; C11D 1/72; C11D 1/90
(52) U.S. Cl. ........................... 510/125; 510/130; 510/135; 510/155; 510/156; 510/235; 510/352; 510/356; 510/421; 510/422; 510/426; 510/427; 510/428; 510/490; 510/237; 510/119; 510/123; 510/127
(58) Field of Search ..................... 510/130, 135, 510/155, 156, 235, 352, 356, 421, 422, 426, 427, 428, 490, 237, 119, 123, 127

(56) References Cited

U.S. PATENT DOCUMENTS

| | | | |
|---|---|---|---|
| 4,426,310 | * | 1/1984 | Verunica ............................... 252/106 |
| 4,948,576 | * | 8/1990 | Verdicchio et al. .................... 424/59 |
| 5,387,375 | * | 2/1995 | Erilli et al. ............................ 252/546 |
| 5,965,502 | * | 10/1999 | Balzer .................................. 510/158 |

FOREIGN PATENT DOCUMENTS

| | | |
|---|---|---|
| 3-130254 | 7/1991 | (JP) . |
| 4-325595 | 11/1992 | (JP) . |
| 5-179285 | 7/1993 | (JP) . |
| 5-506259 | 9/1993 | (JP) . |
| 6-145693 | 5/1994 | (JP) . |
| 6-157243 | 6/1994 | (JP) . |
| 6-509569 | 10/1994 | (JP) . |
| 7-126689 | 5/1995 | (JP) . |
| 1-983537 | 10/1995 | (JP) . |
| 8-48618 | 2/1996 | (JP) . |
| 8-183729 | 7/1996 | (JP) . |
| 8-225441 | 9/1996 | (JP) . |
| 8-508774 | 9/1996 | (JP) . |

* cited by examiner

*Primary Examiner*—Yogendra Gupta
*Assistant Examiner*—Charles Boyer
(74) *Attorney, Agent, or Firm*—Michele G. Mangini

(57) ABSTRACT

A body and hair cleanser composition that is non irritating to the skin and eyes is disclosed. The cleanser composition contains a) a sulfosuccinate anionic surfactant, b) a polyoxyethylene-alkylsulfate anionic surfactant; c) at least one amphoteric surfactant; and d) a polyoxyethylene-sorbitan nonionic surfactant. The weight ratio of sulfosuccinate anionic surfactant to polyoxyethylene-alkylsulfate anionic surfactant is about 1:0.25 to about 1:2, and the weight ratio of sulfosuccinate anionic surfactant to total amount of amphoteric surfactant is about 1:0.25 to about 1:2.

9 Claims, No Drawings

CLEANSER COMPOSITION INCLUDING A MIXTURE OF ANIONIC, NONIONIC, AND AMPHOTERIC SURFACTANTS

FIELD OF THE INVENTION

This invention relates to a cleanser composition, in particular, to shampoo, and further to that of good bubble forming property and low irritating to eye mucous membranes and skin.

BACKGROUND OF THE INVENTION AND PRIOR ART

Conventionally, polyoxyethylene-alkylsulfate-type anionic surfactants are generally used as a main ingredient of cleanser composition, especially, shampoo. The surfactants have been very useful as main components for especially shampoo because of good bubble forming property and good bubble feeling.

However, the shampoo containing polyoxyethylene-alkylsulfate-type anionic surfactants as a main component is irritating to eye mucous membrane or skin, and inappropriate to shampoo for baby or child use.

SUMMARY OF THE INVENTION

The inventor has sought to solve the problems, and accomplished this invention. Thus the present invention relates to a cleanser composition comprising sulfosuccinate-type anionic surfactants; polyoxyethylene-alkylsulfate-type anion surfactants; one or more than two amphoteric surfactants selected from the group consisting of imidazoline-type amphoteric surfactants, amidobetaine-type amphoteric surfactants and alkylbetaine-type amphoteric surfactants; and polyoxyethylene-sorbitan-type nonionic surfactants; characterized by containing, based upon the total weight of the composition: from about 1 to about 15% of sulfosuccinate-type anionic surfactants; from 0.1 to 4% polyoxyethylene-sorbitan-type nonionic surfactants; and wherein:

the weight ratio of sulfosuccinate-type anionic surfactants to polyoxyethylene-alkylsulfate-type anionic surfactants is about 1:0.25 to about 1:2, and the weight ratio of sulfosuccinate-type anionic surfactants to total amount of imidazoline-type amphoteric surfactants, amidobetaine-type amphoteric surfactants and alkylbetaine-type amphoteric surfactants is about 1:0.25 to about 1:2.

DETAILED DESCRIPTION OF PREFERRED EMBODIMENTS

The sulfosuccinate-type anionic surfactants are those synthesized by esterification of one or two carbonic acid group of sulfosuccinic acid by alcohol, and preferably shown by the following formula (A).

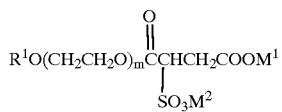

(A)

In this general formula (A), alcohols constructing primary fatty alcohol residues having about 8 to about 22 carbon atoms of $R^1$ are linear or branched saturated or unsaturated alcohols such as octyl alcohol, decyl alcohol, tetradecyl alcohol, hexadecyl alcohol, octadecyl alcohol, eicosyl alcohol and oleyl alcohol, further synthetic alcohol also can be used. m is an integer of 0 to 10, alkaline metals of $M^1$ and $M^2$ are, for example, sodium and potassium, and alkaline earth metals are, for example, magnesium and calcium.

Examples of sulfosuccinate-type anionic surfactants can be disodium polyoxyethylene(3)lauryl sulfosuccinate, disodium polyoxyethylene(2)lauryl sulfosuccinate, disodium polyoxyethylene(3)octyl sulfosuccinate, disodium lauryl sulfosuccinate, disodium polyoxyethylene(3)lauryl sulfosuccinate is in particular preferred.

Examples of polyoxyethylene-alkylsulfate-type anionic surfactants of this invention are surfactants shown by below general formula (B):

$$R^2O(CH_2CH_2O)_nSO_2M^3 \tag{B}$$

where $R^2$ is a primary fatty alcohol residue having about 8 to 22 carbon atoms, $M^3$ is hydrogen atom, an alkaline metal ion, an alkaline earth metal ion or an alkanol amine, and n is an integer of 0 to 10. In preferred compounds of general formula (B), alcohols constructing primary fatty alcohol residues having about 8 to about 22 carbon atoms of $R^2$ are linear or branched saturated or unsaturated alcohols such as octyl alcohol, decyl alcohol, dodecyl alcohol, tetradecyl alcohol, hexadecyl alcohol, octadecyl alcohol, eicosyl alcohol and oleyl alcohol, further synthetic alcohol also can be used. Examples thereof can be sodium polyoxyethylene(2) lauryl sulfate, sodium polyoxyethylene(3) lauryl sulfate, sodium polyoxyethylene(2) dodecylauryl sulfate and triethanolamine polyoxyethylene(2) lauryl sulfate. n is an integer of 0 to 10 and preferably 2 or 3.

Alkaline metals of $M^3$ are, for example, sodium and potassium, and alkaline earth metals are, for example, magnesium and calcium. Alkanol amine can be mono, di or triethanolamine. Preferred examples can be sodium polyoxyethylene(2) lauryl sulfate, sodium polyoxyethylene (3) lauryl sulfate, sodium polyoxyethylene(2) dodecylauryl sulfate and triethanolamine polyoxyethylene(2) lauryl sulfate. More preferred examples are sodium polyoxyethylene (2) lauryl sulfate, sodium polyoxyethylene(3) lauryl sulfate.

Imidazoline-type amphoteric surfactants in this invention are surfactants shown by below general formula (C):

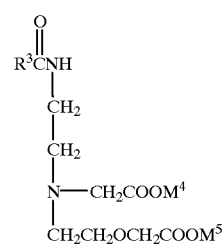

(C)

As preferred imidazoline-type amphoteric surfactants in this invention, alcohols constructing primary fatty alcohol residues having about 8 to about 22 carbon atoms of $R^3$ in general formula (C) are linear or branched saturated or unsaturated alcohols such as octyl alcohol, decyl alcohol, dodecyl alcohol, tetradecyl alcohol, hexadecyl alcohol, octadecyl alcohol, eicosyl alcohol and oleyl alcohol. Alkaline metals of $M^4$, $M^5$ are, for example, sodium and potassium. 2-alkyl-N-carboxymethyl-hydroxyethyl imidazolium betaine can be a specific example.

Amidobetaine-type amphoteric surfactants in this invention are compounds shown by below general formula (D):

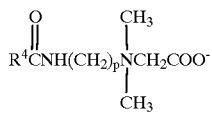

(D)

In the general formula (D) for preferred amidobetaine-type amphoteric surfactants in this invention, alcohols constructing primary fatty alcohol residues having about 8 to about 22 carbon atoms of $R^4$ in general formula (D) are linear or branched saturated or unsaturated alcohols such as cocoyl alcohol, lauryl alcohol, octyl alcohol, decyl alcohol, tetradecyl alcohol, hexadecyl alcohol, octadecyl alcohol, eicosyl alcohol and oleyl alcohol. Coconut oil fatty acid amidopropyl betaine, lauric acid amidopropyl betaine, etc. are preferred, and in particular coconut oil fatty acid amidopropyl betaine are preferred.

Alkylbetaine-type amphoteric surfactants are compounds shown by below general formula (E):

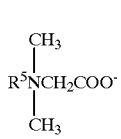

(E)

In the general formula (E) for preferred alkylbetaine-type amphoteric surfactants in this invention, alcohols constructing primary fatty alcohol residues having about 8 to about 22 carbon atoms of $R^5$ in general formula (E) are linear or branched saturated or unsaturated alcohols such as octyl alcohol, decyl alcohol, dodecyl alcohol, tetradecyl alcohol, hexadecyl alcohol, octadecyl alcohol, eicosyl alcohol and oleyl alcohol. Lauryl dimethyl acetate betaine, tetradecyl dimethylamono acetate betaine, etc. are preferred, and in particular lauryldimethylaminoacetate betaine are preferred.

Polyoxyethylene sorbitan nonionic surfactants are compounds shown by below general formula (F):

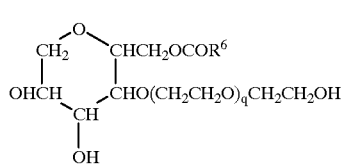

(F)

In the general formula (F) for preferred polyoxyethylene-sorbitan-type nonionic surfactants in this invention, alcohols constructing primary fatty alcohol residues having about 8 to about 22 carbon atoms of $R^6$ in general formula (F) are linear or branched saturated or unsaturated alcohols such as cocoyl alcohol, octyl alcohol, decyl alcohol, dodecyl alcohol, tetradecyl alcohol, hexadecyl alcohol, octadecyl alcohol, eicosyl alcohol and oleyl alcohol. q is preferably about 10 to about 60.

Polyoxyethylene coconut oil fatty acid sorbitan (20), polyoxyethylene coconut oil fatty acid sorbitan (10), oleic acid polyoxyethylene sorbitan (60), etc. are preferred, in particular polyoxyethylene coconut oil fatty acid sorbitan (20) are preferred.

The cleanser composition of this invention contains sulfosuccinate-type anionic surfactants in an amount of about 1 to about 15 weight %, preferably about 3 to about 8 weight %. Sufficient bubble formation is not attained if below about 1 weight %, and there is no effects of addition when exceeding about 15%. The cleanser composition of this invention contains polyoxyethylene-sorbitan-type nonionic surfactants in an amount of about 0.1 to about 4 weight %, preferably about 2 to about 3 weight % in view of bubble forming property and irritating property. Exceeding 4 weight %, bubble forming property decreases, and below about 0.1 weight %, low irritating property cannot be attained.

In the cleanser composition of this invention, the weight ratio of sulfosuccinate-type anionic surfactants to polyoxyethylene-alkylsulfate-type anionic surfactants is about 1:0.25 to about 1:2, preferably about 1:0.3 to about 1:1. When below about 1:0.25, bubble property is not good enough. Exceeding 1:2, also bubble property is not good, and further irritation increases.

In the cleanser composition of this invention, the weight ratio of sulfosuccinate-type anionic surfactants to total amount of imidazoline-type amphoteric surfactants, amidobetaine-type amphoteric surfactants and alkylbetaine-type amphoteric surfactants is about 1:0.25 to about 1:2, and preferably about 1:0.3 to about 1:1. When below about 1:0.25, bubble formation becomes worse, and exceeding 1:2, irritation becomes strong.

The pH of the cleanser composition of this invention is preferably about 4 to about 9, and in particular about 5 to about 8, pH can be controlled using known acidifying agent or alkalifying agent. When the pH is below about 4, skin irritation becomes too strong, and exceeding 9 makes skin goo.

In the cleanser composition of this invention, for example, moisturizers such as fatty acid alkanolamids, silicone derivatives, cationic polymers, propylene glycol, glycerin; viscosity controlling agents such as methyl cellulose, hydroxyethyl cellulose, polyethylene glycol distearate; pearl luster agent, fragrances, pigments, antioxidants, and other additives which usually used for cleansers can be added.

The present invention provides a cleanser, in particular, a shampoo which can be used safely for people sensitive to eye mucous membrane irritation such as baby and child. The cleanser of the present invention has an excellent bubble forming property and fine and delicate bubble property. The compositions of the present invention may be used in shampoos, washes shower gels, baths, and the like.

The low irritating cleanser compositions of this invention will be explained in detail referring to following Examples.

EXAMPLES

Method and Criteria of Evaluation

1. Bubble Forming Property:

Ten subjects are selected, and the respective subjects washed the hair and evaluated bubble forming property. The criteria of the evaluation are as follows:

O: Satisfactory bubble formation.

Δ: A little short of bubble formation.

x: Short of bubble.

2. Bubble Property:

As evaluation of bubble forming property, bubble property was evaluated according to following criteria.

O: Bubble is creamy and comfortable.

Δ: Ordinary bubble and a little short of creamy feeling.

x: Uneven bubble size and inferior bubble feeling.

3. Eye Mucous Membrane Irritation:

Diluting the cleanser up to one tenth of concentration, the irritation was evaluated according to following criteria when one drop of the diluted cleanser is dropped in a subject's eye using a spoit.

O: About the same irritation as purified water.

Δ: A slight irritation but soon disappeared by washing the eye with water.

x: Irritated as soon as dropping was made, and irritation remained for a time after washing the eye with water.

Example 1

Comparative Example 1 to 4

As Example 1, a cleanser composition of following formulation was prepared, Firstly, 985 g purified water was measured and poured into a glass beaker, all the ingredients except for citric acid were measured and added thereto, mixed and uniformly dissolved. Then citric acid was gradually added until the pH of the solution became 7.

| Ingredient | weight/weight % |
|---|---|
| disodium polyoxyethylene(3)lauryl sulfosuccinate | 5.0 |
| Polyoxyethylene coconut oil fatty acid sorbitan (20) | 2.0 |
| Coconut oil fatty acid amidopropyl betaine | 3.0 |
| sodium polyoxyethylene(3)lauryl sulfate | 3.0 |
| polyethyleneglycol distearate | 2.0 |
| fragrance | 0.2 |
| citric acid | adequate amount |
| tetra sodium edetate | 0.2 |
| methylchloro isothiazolinone, methyl isothiazolinone | 0.05 |
| purified water | balance |

Results of evaluations for Example 1 are shown in Table 1. The results show that the cleanser composition of Example 1 is a shampoo of very low irritation to skin and eye mucous membrane, and high bubble forming property. Comparative Example 2 was a cleanser composition prepared as Example 1 except that disodium polyoxyethylene (3)lauryl sulfosuccinate was omitted. The comparative Example 2 showed that, when sulfosuccinate type anionic surfactant is omitted, bubble forming property and bubble property decrease and eye mucous membrane irritation deteriorated. Comparative Example 1 was a cleanser composition prepared as Example 1 except that sodium polyoxyethylene(3)lauryl sulfate was omitted and disodium polyoxyethylene(3)lauryl sulfosuccinate was replaced by disodium polyoxyethylene(2)lauryl sulfosuccinate, which showed that bubble forming property and bubble property decreased when polyoxyethylene-alkyl-sulfate-type surfactant was omitted.

Similarly, Comparative Example 3 was a cleanser composition prepared as Example 1 except that polyoxyethylene coconut oil fatty acid sorbitan (20) was omitted and disodium polyoxyethylene(3)lauryl sulfosuccinate was replaced by disodium polyoxyethylene(2)lauryl sulfosuccinate, which shows that eye mucous membrane irritating property deteriorates when polyoxyethylene sorbitan type surfactant is omitted.

Further, Comparative Example 4 was a cleanser composition prepared as Example 1 except that no betaine type amphoteric surfactant was added, which showed that balance of properties as cleanser shifts and bubble forming property, bubble property and eye mucous membrane irritating property were all insufficient.

Contents of main ingredients for respective Examples and their evaluation results are listed in Table 1. All the Examples further include 0.2% fragrant, 0.2% tetrasodium edetate, and 0.05% methylchloro isothiazolinone and methyl isothiazolinone. The examples all retain preferable properties as cleanser composition.

TABLE 1

|  | Example | | | | | | | | | | Comparative Example | | | |
|---|---|---|---|---|---|---|---|---|---|---|---|---|---|---|
|  | 1 | 2 | 3 | 4 | 5 | 6 | 7 | 8 | 9 | 10 | 1 | 2 | 3 | 4 |
| Sodium POE (2) lauryl sulfate | — | — | — | — | — | — | — | 3 | 3 | — | — | — | — | — |
| Sodium POE (3) lauryl sulfate | 3 | 2 | 3 | 3 | 4 | 3 | 3 | — | — | 3 | — | 3 | 3 | 3 |
| Disodium POE (2) lauryl sulfosuccinate | — | — | — | — | — | — | — | 5 | — | 5 | — | 5 | 5 | |
| Disodium POE (3) lauryl sulfosuccinate | 5 | 5 | 5 | 5 | 4 | 4 | 4 | 5 | — | — | — | — | — | — |
| Disodium POE lauryoyl-ethanol-amide sulfosuccinate | — | — | — | — | — | — | — | — | 5 | — | — | — | — | — |
| POE coconut oil fatty acid sorbitan (20) | 2 | — | — | — | — | — | — | 2 | 2 | 2 | 2 | 2 | — | 2 |
| POE sorbitan oleate (20) | — | 2 | 2 | 2 | 2 | 4 | 2 | — | — | — | — | — | — | — |
| Coconut oil fatty acid amidopropyl betaine | 3 | — | — | — | — | — | — | — | — | — | 3 | 3 | 3 | — |

TABLE 1-continued

| | Example | | | | | | | | | | Comparative Example | | | |
|---|---|---|---|---|---|---|---|---|---|---|---|---|---|---|
| | 1 | 2 | 3 | 4 | 5 | 6 | 7 | 8 | 9 | 10 | 1 | 2 | 3 | 4 |
| 2-alkyl-carboxymethyl-N-hydroxy-ethyl-imidazolinium betaine | — | — | — | — | — | — | — | — | — | 3 | — | — | — | — |
| Lauryl-dimethyl-aminoacetate betaine | — | 3 | 3 | 2 | 3 | 3 | 3 | 3 | 3 | — | — | — | — | — |
| POE distearate | 2 | 2 | 2 | 2 | 2 | 2 | 2 | 2 | 2 | 2 | 2 | 2 | 2 | 2 |
| Citric acid | A. Am | A. Am | A. Am | A. Am | A. Am | A. Am | A. Am | A. Am | A. Am | A. Am | A. Am | A. Am | A. Am | A. Am |
| Purified water | Bl. | Bl. | Bl. | Bl. | Bl. | Bl. | Bl. | Bl. | Bl. | Bl. | Bl. | Bl. | Bl. | Bl. |
| Bubble forming property | ◯ | ◯ | ◯ | ◯ | ◯ | ◯ | ◯ | ◯ | ◯ | ◯ | x | x | ◯ | Δ |
| Bubble property | ◯ | ◯ | ◯ | ◯ | ◯ | ◯ | ◯ | ◯ | ◯ | ◯ | x | x | ◯ | Δ |
| Eye mucous membrane irritation | ◯ | ◯ | ◯ | ◯ | ◯ | ◯ | ◯ | ◯ | ◯ | ◯ | ◯ | Δ | x | Δ |
| PH | 7 | 7 | 7 | 7 | 7 | 7 | 7 | 7 | 7 | 7 | 7 | 7 | 7 | 7 |

A. Am: Adequate amount
Bl.: Balance

Examples 11 to 13

Comparative Examples 5 and 6

Disodium polyoxyethylene(3)lauryl sulfosuccinate was used for the sulfosuccinate type anionic surfactant, the amounts of which were changed from 0.5 weight % (Comparative Example 5) up to 20 weight % (Comparative Example 6), and further proper proportional changes were made for each sample, cleanser compositions shown in Table 2 were prepared and the properties for each sample were measured. As a result, when the amount of sulfosuccinate type anionic surfactant is from 1 weight % (Example 11) to 15 weight % (Example 13), all the properties measured were preferred. On the other hand, bubble forming property and bubble property were not satisfactory in Comparative Example 5 which contains 0.5 weight %, and bubble property and eye mucous membrane irritation property is not satisfactory in Comparative Example 6 containing 20 weight %. The results show that preferred properties can be obtained when the amount of sulfosuccinate type anionic surfactant is within the range from 1 weight % to 15 weight %.

Examples 14

Comparative Examples 7 and 8

Cleanser compositions shown in Table 2 were prepared by changing the amount of polyoxyethylene sorbitan type nonionic surfactant to 0.05%, 1% and 6% respectively and further proper proportional changes were made for respective samples, and the properties for the samples were measured. As a result, when the amount was 0.1 weight %, evaluations were preferable. However in 0.05 weight %, eye mucous membrane irritating property was not good (Comparative Example 7). When containing 6 weight %, foamability deteriorated, and bubble forming property and bubble property were not satisfactory. Summarizing these results and those of above Examples 1 to 10, preferred property could be obtained when the amount of polyoxyethylene sorbitan type nonionic surfactant is within the range from 0.1 weight % to 4 weight %.

Examples 15

Comparative Examples 9 and 10

The weight ratios of sulfosuccinate-type anionic surfactant to polyoxyethylene-alkylsulfate-type anionic surfactant were changed to about 1:0.14, 1:0.33, 1:2.2 and the properties for the samples were measured. Further considering the results of above Examples 11 to 13, preferred properties can be obtained when the weight ratios of sulfosuccinate-type anionic surfactant to polyoxyethylene-alkylsulfate-type anionic surfactant were within the range from 1:0.25 (Example 13) to 1:2 (Example 11), however bubble property was not good when the ratio was lower than 1:0.25 (Comparative Example 9), and eye mucous membrane irritating property deteriorated when exceeding 1:2 (Comparative Example 10).

Examples 16

Comparative Examples 11 and 12

The weight ratio of sulfosuccinate-type anionic surfactant to total amount of imidazoline-type amphoteric surfactants, amidobetaine-type amphoteric surfactants and alkylbetaine-type amphoteric surfactants was changed to about 1:0.14, 1:0.33, 1:2.2 and the properties for the samples were measured. Further considering the results of above Examples 11 to 13, preferred properties can be obtained when the weight ratio of sulfosuccinate type anionic surfactant to a total amount of above-said amphoteric surfactants is within the range from 1:0.25 (Example 13) to 1:2 (Example 11), however bubble forming property and bubble property were not good when the ratio was lower than 1:0.25 (Comparative Example 11), and bubble property and eye mucous membrane irritating property deteriorated when exceeding 1:2 (Comparative Example 12).

Examples 17 to 19

The effects to the properties were investigated for several kinds of amphoteric surfactants, and as a result preferred properties were obtained for all the amphoteric surfactant examined.

TABLE 2

| | Examples | | | | | | | | | Comparative Examples | | | | | | | |
|---|---|---|---|---|---|---|---|---|---|---|---|---|---|---|---|---|---|
| | 11 | 12 | 13 | 14 | 15 | 16 | 17 | 18 | 19 | 5 | 6 | 7 | 8 | 9 | 10 | 11 | 12 |
| Sulfosuccinate-type surfactant (A) | 2 | 10 | 15 | 5 | 6 | 6 | 4 | 4 | 4 | 0.5 | 20 | 5 | 5 | 7 | 2.5 | 7 | 2.5 |
| POE alkylsulfate-type Sf. (B) | 3 | 3 | 3.75 | 3 | 2 | 3 | 3 | 3 | 3 | 3 | 5 | 3 | 3 | 1 | 5.5 | 3 | 3 |
| Imidazolinium betaine (D) | 0 | 0 | 0 | 0 | 0 | 0 | 4 | 0 | 0 | 0 | 0 | 0 | 0 | 0 | 0 | 0 | 0 |
| Amidopropyl betaine (C) | 4 | 3 | 3.75 | 4 | 4 | 2 | 0 | 4 | 0 | 4 | 4 | 4 | 4 | 4 | 4 | 1 | 5.5 |
| Lauryldimethylamino-acetate betaine (E) | 0 | 0 | 0 | 0 | 0 | 0 | 0 | 0 | 4 | 0 | 0 | 0 | 0 | 0 | 0 | 0 | 0 |
| POE-sorbitan type Sf. (F) | 3 | 3 | 3 | 0.1 | 3 | 3 | 3 | 3 | 3 | 3 | 3 | 0.05 | 6 | 3 | 3 | 3 | 3 |
| PEG distearate | 2 | 2 | 2 | 2 | 2 | 2 | 2 | 2 | 2 | 2 | 2 | 2 | 2 | 2 | 2 | 2 | 2 |
| Citric acid | A. Am. | A. Am. | A. Am. | A. Am | A. Am. | A. Am. | A. Am. | A. Am. | A. Am. | A. Am. | A. Am. | A. Am. | A. Am. | A. Am. | A. Am. | A. Am. | A. Am. |
| Property: | | | | | | | | | | | | | | | | | |
| Bubble forming property | ○ | ○ | ○ | ○ | ○ | ○ | ○ | ○ | ○ | Δ | ○ | ○ | x | ○ | ○ | ○ | ○ |
| Bubble property | ○ | ○ | ○ | ○ | ○ | ○ | ○ | ○ | ○ | Δ | Δ | ○ | x | Δ | ○ | Δ | Δ |
| Eye mucous membrane irritation | ○ | ○ | ○ | ○ | ○ | ○ | ○ | ○ | ○ | ○ | Δ | x | ○ | ○ | x | ○ | Δ |
| PH | 7 | 7 | 7 | 7 | 7 | 7 | 7 | 7 | 7 | 7 | 7 | 7 | 7 | 7 | 7 | 7 | 7 |

Sf.: surfactant.
A. Am.: Adequate amount

What is claimed is:

1. A cleanser composition comprising: a) a sulfosuccinate anionic surfactant, b) a polyoxyethylene-alkylsulfate anionic surfactant; c) at least one amphoteric surfactant selected from the group consisting of imidazoline amphoteric surfactants, amidobetaine amphoteric surfactants and alkylbetaine amphoteric surfactants; and d) a polyoxyethylene-sorbitan nonionic surfactant;

characterized by containing, based upon the total weight of the composition: from about 3% to about 15% sulfosuccinate anionic surfactant; and from about 0.1% to about 4% polyoxyethylene-sorbitan nonionic surfactants; wherein:

the weight ratio of sulfosuccinate anionic surfactants to polyoxyethylene-alkylsulfate anionic surfactants being about 1:0.25 to about 1:2, and the weight ratio of sulfosuccinate anionic surfactants to total amount of imidazoline amphoteric surfactants, amidobetaine amphoteric surfactants and alkylbetaine amphoteric surfactants being about 1:0.25 to about 1:2.

2. The cleanser composition according to claim 1 wherein sulfosuccinate anionic surfactants are surfactants of the general formula (A):

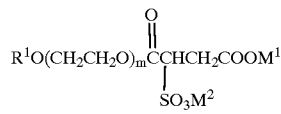

(A)

wherein $R^1$ is a primary fatty alcohol residue having about 8 to about 22 carbon atoms, m is an integer of 0 to about 20, $M^1$ and $M^2$ are each independently hydrogen atom, an alkaline metal ion or an alkaline earth metal ion.

3. The cleanser composition according to claim 1 wherein polyoxyethylene-alkylsulfate anionic surfactants are surfactants of the general formula (B):

wherein $R^2$ is a primary fatty alcohol residue having about 8 to about 22 carbon atoms, $M^3$ is hydrogen atom, an alkaline metal ion, an alkaline earth metal ion or an alkanol amine, and n is an integer of 0 to about 10.

4. The cleanser composition according to claim 1 wherein imidazoline amphoteric surfactants are surfactants of the general formula (C):

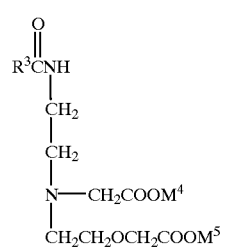

wherein $R^3$ is a primary fatty alcohol residue having about 8 to 22 carbon atoms, and $M^4$ and $M^5$ are each independently hydrogen atom, an alkaline metal ion or an alkaline earth metal ion.

5. The cleanser composition according to claim 1 wherein amidobetaine amphoteric surfactants are surfactants of the general formula (D):

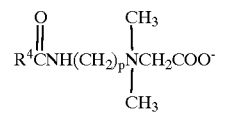

wherein $R^4$ is a primary fatty alcohol residue of having about 8 to about 22 carbon atoms, and p is an integer of 1 to about 18.

6. The cleanser composition according to claim 1 wherein alkylbetaine amphoteric surfactants are surfactants of the general formula (E):

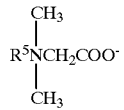
(E)

wherein $R^5$ is a primary fatty alcohol residue having about 8 to about 22 carbon atoms.

7. The cleanser composition according to claim 1 wherein (b) polyoxyethylene-sorbitan nonionic surfactants are surfactants of the general formula (F):

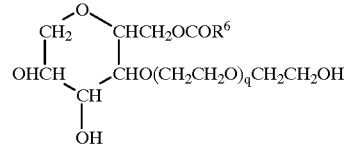
(F)

wherein $R^6$ is a primary fatty alcohol residue having about 8 to about 22 carbon atoms, and q is an integer of 0 to about 60.

8. The cleanser composition according to claim 1 wherein the cleanser composition is a shampoo, gel, personal bath composition, or body wash.

9. The cleanser composition of claim 1 wherein the composition is low irritating to the eye mucous membranes and skin.

* * * * *